US007979129B2

(12) United States Patent
Gill

(10) Patent No.: US 7,979,129 B2
(45) Date of Patent: Jul. 12, 2011

(54) DEEP BRAIN STIMULATION OF THE ZONA INCERTA

(75) Inventor: Steven Streatfield Gill, Bristol (GB)

(73) Assignee: Medtronic Inc., Minneapolis, MN (US)

( * ) Notice: Subject to any disclaimer, the term of this patent is extended or adjusted under 35 U.S.C. 154(b) by 1202 days.

(21) Appl. No.: 11/146,738

(22) Filed: Jun. 7, 2005

(65) Prior Publication Data

US 2005/0277995 A1 Dec. 15, 2005

(30) Foreign Application Priority Data

Jun. 11, 2004 (GB) .................................. 0413076.1

(51) Int. Cl.
*A61N 1/00* (2006.01)
(52) U.S. Cl. ........................................................ 607/45
(58) Field of Classification Search ................ 607/45
See application file for complete search history.

(56) References Cited

U.S. PATENT DOCUMENTS

2004/0225335 A1* 11/2004 Whitehurst et al. ............. 607/45

FOREIGN PATENT DOCUMENTS

| EP | 0 832 667 A2 | 9/1997 |
|---|---|---|
| EP | 1 062 973 A1 | 8/1999 |
| WO | WO 99/36122 | 7/1999 |
| WO | WO 00/33625 | 6/2000 |

OTHER PUBLICATIONS

Hamel, W. et al., "Deep Brain Stimulation of the Subthalamic Nucleus in Parkinson's Disease: Evaluation of Active Electrode Contacts," *J Neurol Neurosurg Psych*, 74:1036-1046 (2003).

Herzog, Jan et al., "Most Effective Stimulation Site in Subthalamic Deep Brain Stimulation for Parkinson's Disease," *Movement Disorders*, vol. 19, No. 9, 1050-1099 (2004).

Kolmac, Christian I. et al., "Patterns of Connections Between Zona Incerta and Brainstem in Rats," *Journal of Comparative Neurology*, 396:544-555 (1998).

Lanotte, M.M. et al., "Deep Brain Stimulation of the Subthalamic Nucleus: Anatomical, Neurophysiological, and Outcome Correlations with the Effects of Stimulation," *J. Neuol Neurosurg Psychiatry*, 72:53-58 (2002).

Lin, R.C.S. et al., Topographic and Laminar Organizations of the Incertocortical Pathway in Rats, *Neuroscience*, vol. 81:3; 641-651 (1997).

May, P.J. et al., "Reciprocal Connections Between the Zona Incerta and the Pretectum and Superior Colliculus of the Cat," *Neuroscience*, vol. 77:4; 1091-1114 (1997).

Merello, Marcelo, et al., "Neuronal Activity of the Zona Incerta in Parkinson's Disease Patients," *Movement Disorders*, vol. 21:7; 937-943 (2006).

Mitrofanis, J., "Some Certainty for the "Zone of Uncertainty"? Exploring the Function of the Zona Incerta," *Neuroscience*, 130:1-15 (2005).

Mitrofanis, John et al., "Chemoarchitectonic Heterogeneities in the Primate Zona Incerta: Clinical and Functional Implications," *Journal of Neurocytology*, 33:429-440 (2004).

(Continued)

*Primary Examiner* — Scott M Getzow
(74) *Attorney, Agent, or Firm* — Campbell Nelson Whipps LLC

(57) ABSTRACT

That deep brain stimulation can be used in the treatment of movement disorders and for identifying an area of the brain to be targeted by DBS in the treatment of movement disorders.

5 Claims, 3 Drawing Sheets

OTHER PUBLICATIONS

Mitrofanis, John et al., "Organisation of the Cortical Projection to the Zona Incerta of the Thalamus," *The Journal of Comparative Neurology*, 412:173-185 (1999).

Mogenson, G.J. et al., "Evidence that Projections from Substantia Innominata to Zona Incerta and Mesencephalic Locomotor Region Contribute to Locomotor Activity," *Brain Research*, 334:65-76 (1985).

Mundinger, F. "Stereotaxic Interventions on the Zona Incerta Area for Treatment of Extrapyramidal Motor Disturbances and their Results," 2$^{nd}$ *Int. Symp. Stereoencephalotomy*, 26:222-230 (1965).

Patel, Nikunj K. et al., "MRI-Directed Subthalamic Nucleus Surgery for Parkinson's Disease," *Stereotact Funct Neurosurg.*, 78:132-145 (2002).

Patel, Nikunj K. et al., "Unilateral Subthalamotomy in the Treatment of Parkinson's Disease," *Brain*, 126:1 136-1145 (2003).

Patel, N. K: et al., "MRI Directed Bilateral Stimulation of the Subthalamic Nucleus in Patients with Parkinson's Disease," *J. Neurol Neurosurg Psychiatry*, 74:1631-1637 (2003).

Plaha, Puneet et al., "Stimulation of the Subthalamic Region for Essential Tremor," *J. Neurosurg.*, 101-48-54 (2004).

Power, Brian D. et al., "Evidence for a Large Projection from the Zona Incerta to the Dorsal Thalamus," *The Journal of Comparative Neurology*, 404:554-565 (1999).

Power, Brian D. et al., "Evidence for a Visual Subsector Within the Zona Incerta," *Visual Neuroscience*, 18:179-186 (2001).

Power, Brian D. et al., "Ultrastructure of Afferents from the Zona Incerta to the Posterior and Parafascicular Thalamic Nuclei of Rats," *The Journal of Comparative Neurology*, 451:33-4 (2002).

Roger, Michel et al., "Afferents to the Zona Incerta in the Rat: A Combined Retrograde and Anterograde Study," *The Journal of Comparative Neurology*, 241:480-492 (1985).

Shammah-Lagnado, S.J. et al., "Afferent Connections of the Zona Incerta: A Horseradish Peroxidase Study in the Rat," *Neuroscience*, 15:1, 109-134 (1985).

Tonelli, Leonardo et al., "Dopaminergic Neurons in the Zona Incerta Modulates Ingestive Behavior in Rats," *Physiology & Behavior*, 58:4, 725-729 (1995).

Voges, Jürgen, et al., "Bilateral High-Frequency Stimulation in the Subthalamic Nucleus for the Treatment of Parkinson Disease: Correlation of Therapeutic Effect with Anatomical Electrode Position," *J. Neurosurg.*, 96:269-279 (2002).

Yokoyama Tetsuo, et al., "The Optimal Stimulation Site for Chronic Stimulation of the Subthalamic Nucleus in Parkinson's Disease," *Stereotactic Functional Neurosurgery*, 77:61-67 (2001).

Benabid, A. et al., "Chronic electrical stimulation of the ventralis intermedius nucleus of the thalamus as a treatment of movement disorders," *J. Neuro.* 84:203-214 (1996).

Benabid, A. et al., "Long-term suppression of tremor by chronic stimulation of the ventral intermediate thalamic nucleus," *Lancet*, 337:403-06 (1991).

Berney, A. et al., "Effect on mood of subthalamic DBS for Parkinson's disease A consecutive series of 24 patients," *Am. Acad. Of Neur.* 59(9), 1427-1429 (2002).

Constantino, A. et al., "Unilateral disappearance of essential tremor after cerebral hemispheric infarct," *J. Neurol.* 250:354-355 (2003).

De Zeeuw, C. et al., "Microcircuitry and function of the inferior olive," *TINS*, 21:391-400 (1998).

Deuschl, G. et al., "The pathophysiology of essential tremor," *Neurology*, 54 (Supp. 4), S14-S20 (2000).

Duncan, R. et al., "Essential tremor cured by infarction adjacent to the thalamus," *J. Neurol Neurosurg. Psych.*, 591-592 (1988).

Dupuis, M. et al., "Homolateral Disappearance of Essential Tremor After Cerebellar Stroke," Movement Disorders, 4:2, 183-187 (1989).

Elble, R., "Central Mechanisms of Tremor," *Journal of Clinical Neuro.*, 13(2):133-144 (1996).

Goldman, M. et al., "The symptomatic and functional outcome of stereotactic thalamotomy for medically intractable essential tremor," *J. Neurosurg.* 76:924-928 (1992).

Hariz, M. et al., "Tolerance and Tremor Rebound following Long-Term Chronic Thalamic Stimulation for Parkinsonian and Essential Tremor," *Stereotact Funct Neurosurg.* 72:208-218 (1999).

Jankovic, J. et al., "Outcome after Stereotactic Thalamotomy for Parkinsonian, Essential, and Other Types of Tremor," *Neurosurgery*, 37:4, 680-687 (1995).

Mohadjer, M. et al., "Long-Term Results of Stereotaxy in the Treatment of Essential Tremor," *Stereotact Funct Neurosurg.* 54-55:125-129 (1990).

Houeto, J.L. et al., "Behavioural disorders, Parkinson's disease and subthalamic stimulation," *Journal of Neurology Neurosurgery and Psychiatry*, 72:701-707 (2002).

Kulisevsky, J. et al., "Mania following deep brain stimulation for Parkinson's diseaase," *Neurology*, 59(9), 1421-1424 (2002).

Murata, J. et al., "Electrical stimulation of the posterior subthalamic area for the treatment of intractable proximal tremor," *J. Neurosurg.* 99:708-715 (2003).

Nagaratnam, N. et al., "Contralateral abolition of essential tremor following a pontine stroke," *J. of Neur. Sci.* 149:195-196 (1997).

Nagaseki, Y. et al., "Long-term follow-up results of selective VIM-thalamotomy," *J. Neurosurg.* 65:296-302 (1986).

Ondo, W. et al., "Thalamic Deep Brain Stimulation: Effects on the Nontarget Limbs," *Movement Disorders*, 16:6, 1137-1142 (2001).

Pahwa, R. et al., "Bilateral thalamic stimulation for the treatment of essential tremor," *Neurology*, 53:1447-1450 (1999).

Rajput, A.H. et al., "Clinicopathologic observations in essential tremor: Report of six cases," *Neurology*, 41:1422-1424 (1991).

Rossitch, E. et al., "Evaluation of Memory and Language Function Pre- and Postthalamotomy with an Attempt to Define Those Patients at Risk for Postoperative Dysfunction," *Surg. Neurol.* 29:11-6 (1988).

Schuurman, R. et al., "A Comparison of Continuous Thalamic Stimulation and thalamotomy for Suppression of Severe Tremor," *N. Engl Med.*, 342:7, 461-8 (2000).

Selby, G., "Stereotactic Surgery for the Relief of Parkinson's Disease Part 2. An Analysis of the Results in a Series of 303 Patients (413 Operations)," *J neur Sci.*, 5:343-375 (1967).

Taha, J. et al., "Thalamic deep brain stimulation for the treatment of head, voice, and bilateral limb tremor," *J Neurosurg* 91:68-72 (1999).

Tasker, R. et al., "Deep Brain Stimulation and Thalamotomy for Tremor Compared," *Acta Neurochir.* [Suppl] 68:49-53 (1997).

Wilms, H. et al., "Animal Models of Tremor," *Movement Disorders*, 14:4, 557-571 (1999).

Voges, Jurgen, et al; Bilateral High-Frequency Stimulation in the Subthalamic Nucleus for The Treatment of Parkins Disease. J Neurosurg 96: 269-272 (2002).

Benazzous, Abdelhamid, et al; High-Frequency Stimulation of Both Zona Incerty and Subthalamic Nucleus Induces a Normalization of Basal Ganglia Metabolic Activity in Experimental Parkinsonism. The FASEB Journal express article 10.1096/fj.03-0576fje. Published online Jan. 8, 2004.

* cited by examiner

DEEP BRAIN STIMULATION OF THE ZONA INCERTA

CROSS-REFERENCE TO RELATED APPLICATIONS

This application claims the benefit of priority of GB 0413076.1, filed 11 Jun. 2004, which is incorporated herein by reference.

BACKGROUND OF THE INVENTION

1. Field of the Invention

The present invention relates to a method for treating movement disorders using deep brain stimulation (DBS), and to a method of identifying an area of the brain to be targeted by DBS in the treatment of movement disorders.

2. Description of Related Art

Movement disorders refer to a number of conditions including Hypokinesia (Parkinson's disease), Hyperkinetic disorders (L-dopa induced dyskinesia, Hemiballism and Chorea), Dystonia (generalized and localized) and Tremor (Resting, Postural and Action tremor).

Parkinson's disease (PD) is a chronic, progressive neurodegenerative movement disorder. The main symptoms are tremors, rigidity, slow movement (bradykinesia), poor balance and difficulty walking. The highest prevalence of PD is in Europe and North America with around 1 to 1.5 million people being affected in the USA. Caucasian populations are affected more than others, with a prevalence of around 120-180 per 100,000 people. Symptoms of PD may appear at any age, but the average age of onset is 60. PD is rare in young people and risk increases with age. The cause of the disease is unknown, but there may be genetic factors.

PD is associated with degeneration of several neuronal modulators in the midbrain that primarily affect the motor system. These include the midbrain dopaminergic nuclei, the serotoninergic median raphe nuclei, the noradrenergic locus coeruleus and the cholinergic pedunculopontine nucleus.

At present, there is no cure for PD. Medical treatment for PD relies on a variety of drugs that stimulate dopamine receptors and although this approach may be effective for 5-10 years, therapy is complicated by motor side effects including "on/off" fluctuations and dyskinesias. With progressive degeneration of the dopaminergic system and other neuronal modulators the patient develops fluctuating responses to medical intervention. Surgery may be contemplated in patients who are poorly controlled on best medical therapy.

Hyperkinetic Disorders are sudden rapid involuntary and purposeless movements that typically intrude into the patient's normal activity. These movements may be both axial and peripheral. Examples of hyperkinetic disorders include L-Dopa dyskinesia, which is a complication of PD, Chorea and Hemiballism, which may result from brain lesions involving the basal ganglia. There are no effective medical treatments for these conditions.

Dystonia is a postural disorder characterized by involuntary muscle contractions affecting various parts of the body including the limbs, trunk, shoulders, face and neck.

Tremor is involuntary oscillatory movements produced by alternating contractions of agonist and antagonist muscles. These movements can affect the proximal and distal limb muscles and also the axial muscle groups. Tremor can occur at rest, with the limb maintained in a particular posture and/or during movements. Tremor can occur as a sign of PD, and as a result of lesions of the basal ganglia, midbrain or the cerebellum, but its most common form is familial Essential Tremor (ET). Medical treatments tend to variably suppress rather than abolish tremor.

At present there are various surgical treatments available for movement disorders; however, many of them involve side effects. Movement disorders are due to abnormal patterns of neuronal firing permeating the motor pathways. Surgical treatment aims to disrupt the transmission of these abnormal patterns by destroying or lesioning motor pathways or nuclei or alternatively overriding the abnormal patterns with high frequency electrical stimulation. The latter treatment is known as Deep Brain Stimulation (DBS) and is achieved by implanting an electrode into the pathways or nuclei in the brain and delivering pulsed electrical current to the tissue from an implanted pulse generator which is connected to the electrode.

A number of targets are known to be effective in the treatment of movement disorders. These include the Globus Pallidus Internus (Gpi), the Ventral Intermediate Nucleus (Vim) of the thalamus and the Subthalamic Nucleus (STN).

Lesions or DBS of the Gpi are effective for the treatment of PD, Dystonia and Hyperkinetic movements. This type of treatment has a modest effect on PD symptoms such as tremor, rigidity, bradykinesia and akinesia, but is effective in treating the motor side effects of L-dopa therapy such as dyskinesia and dystonia which allow the patient to continue on a high dose of medication.

Bilateral Gpi lesions/DBS are associated with worsening axial symptoms including deterioration in speech, swallowing and gait.

Lesions or DBS of the Vim are effective for the treatment of PD tremor but do not affect other symptoms of PD. Typically the Ventralis Intermedius (Vim) nucleus of the thalamus is the target of choice for the treatment of ET. Lesioning is reported to provide good contralateral tremor suppression. However recurrence may occur within weeks or years and long-term studies show that significant tremor persists in 17-32% of cases, (1-5). Bilateral lesions are associated with significant complications including permanent speech impairment in over 25% and memory and language dysfunction in over 50% of cases (5, 6).

Clinical studies suggest that DBS of Vim is as effective as lesioning in controlling ET (7, 8) but is likewise associated with side effects, particularly when carried out bilaterally with 30-50% patients suffering from dysarthria and dysequilibrium, (9-13) However the adverse effects associated with DBS are generally reversible by adjusting the stimulation parameters, though this may be that the expense of satisfactory tremor control. Patients treated with DBS are also reported to develop tolerance (habituation) to stimulation, despite increasing its amplitude. Patients are advised to turn the stimulators "off" at night and take stimulation holidays for weeks, in order to prevent tissue habituation, (2, 3, 14).

Lesioning of the subthalamic nucleus is known to improve tremor, rigidity, bradykinesia and akinesia and allows patients to reduce their medications, which in turn enables patients to reduce their medication. However, the Subthalamic nucleus is a small structure measuring 12 mm antero-posteriorly, 3 mm in width and 6 mm dorso-ventrally; and misplacement of a lesion can cause significant and permanent side effects. As a result, most centers prefer to implant DBS electrodes into the STN because side effects are generally reversible by reducing or stopping stimulation. DBS of the STN is currently the surgical treatment of choice for PD, nevertheless it is not without side-effects. Houeto et al., reported worsening of anxiety and depression following DBS of STN with a prevalence of anxiety in 75% of patients (15).

Berney et al., reported that DBS of STN can provoke depression in 25% with several having suicidal tendencies (16). Mania has also been reported (17). Some groups have, in addition, reported worsening of speech.

In addition to motor functions, the STN has limbic and associative functions. Disruption of these with DBS may contribute to worsening anxiety and depression seen with this treatment. Medial to the STN are fibers carrying cerebellar information to the thalamus and spread of current to these may interfere with information regarding precision movements of the larynx and hence cause worsening of speech. Stimulation of structures anterior and ventral to the subthalamic nucleus including the substantia nigra and area of Sano are associated with severe depression and mania/rage respectively.

Although bilateral simulation of the subthalamic nucleus (STN) is currently regarded as the optimum target by many neurosurgical centers the most effective therapeutic contact on a quadripolar DBS lead transfixing the STN has been reported as being one positioned at the interface of the dorsal surface of the STN and the adjacent white matter tracts (1).

Murata et al., (27) describe stimulating the posterior subthalamic area for treating proximal tremor. The treatment area selected by Murata et al. is particularly close to the prelemniscal radiation. Stimulation of this area can result in severe side effects such as speech disturbances, difficulty with precision movements and postural problems The inventor has found that movement disorders can be treated by using DBS on a part of the brain which has not previously been targeted. This treatment avoids at least some of the problems associated with some of the prior art methods.

SUMMARY OF THE INVENTION

In accordance with the invention, there is provided a method for treating movement disorders comprising the step of applying deep brain stimulation to the caudal zona incerta (ZI) of the brain.

The ZI is a layer of grey matter located ventral to the thalamus and is dorso-medial and caudal to the STN. The term "zona incerta" is well known to those skilled in the art. Running between the dorsal and medial aspect of the STN and the ZI are the pallidofugal fibers from the Gpi to the Ventralis anterior (VA) nucleus of the thalamus. Medial to ZI are Cerebello-thalamic fibers separating it from the red nucleus and posteriorly runs the medial lemniscus carrying sensory fibers from the dorsal columns to the Ventro-posterior (VP) nucleus of the thalamus. The ZI receives input from the basal ganglia, the reticular activating system (RAS), Substantia Nigra Compacta and the associative and limbic areas of the brain, which facilitate and modulate motor behavior. The ZI outputs to the centromedian and parafascicular nuclei of the thalamus, the basal ganglia and also to the cortex and locomotor centers in the brain stem.

Without being bound to a particular theory, it is generally thought that the ZI facilitates and augments particular motor tasks under the influence of the limbic system which directs nonspecific excitation from the RAS received by ZI, to specific areas of the intralaminar nuclei of the thalamus, the cortex and the midbrain extrapyramidal area (MEA). The intralaminar nuclei and in particular the CM/Pf in turn excite specific areas in the basal ganglia so that they can also process information. For information processing to occur in the brain, participating neurons need to oscillate in synchrony at high frequency and information is then seen as bursts of firing occurring between clusters of neurons that can be transmitted to other neurons oscillating in phase. Non participating neurons will fire irregularly at variable frequencies. The CM/Pf is important in generating synchronous oscillations in specific areas of the basal ganglia, and the basal ganglia play an important role in transmitting these oscillations to relevant areas of the cortex thereby making them available for information processing.

Preferably the movement disorder is selected from the group consisting of Hypokinesia, Hyperkinetic disorders, Dystonia and Tremor. In particular the movement disorder may be Parkinson's disease or Essential tremor. Preferably the movement disorder is Parkinson's disease.

It is currently understood that in idiopathic Parkinson's Disease (PD) neuronal loss from the Substantia Nigra pars compacta (SNc) affects dopamine delivery to the sensory motor putamen, but there is also a variable reduction of dopamine delivery to GPi/SNr, STN and ZI.

Loss of dopamine delivery to the Striatal and Gpe neurons makes them more resistant to generating high frequency oscillations and burst firing and the asynchronous basal ganglia output is maintained. Thus, thalamocortical neurons which receive basal ganglia afferents cannot synchronize the frontal cortex to the higher frequency range which prevents efficient information processing resulting in akinesia and bradykinesia.

In tremor predominant disease there is more specific dopamine loss to presynaptic STN/ZI neurons, which results in excessive release of glutamate from their cortical and CM/Pf afferents. The rate of release of glutamate is governed by the dominant frequency in the motor cortex which, unable to generate synchronized high frequencies is maintained in the low frequency range of ~20 Hz. STN/ZI will therefore tend to burst fire at ~20 Hz and produce abnormal low frequency synchronization of the basal ganglia output, which may be augmented by concomitant loss of serotonin which has also been found in tremor predominant PD patients. The ZI projects to the interpositus nucleus and in turn the interpositus nucleus heavily projects to the ZI and the Vim nucleus of the thalamus. Low frequency oscillations arriving in the Vim nucleus neurons, in the presence of low levels of serotonin may burst fire in the 4-8 Hz range and this will be manifested as tremor of the peripheral limbs on reaching the motor cortex.

High frequency stimulation of the ZI above 80 Hz will override low frequency 20 Hz synchronous oscillations and synchronize the basal ganglia output and in turn the thalamocortical neurons as well as MEA in the high frequency range, abolishing tremor and facilitating cortical and brainstem information processing and improving the symptoms of Parkinson's disease.

The etiology of ET is poorly understood. Although no morphological changes have been identified (18) it has been attributed to a functional disturbance in the inferior olivary nucleus, where abnormally synchronized 4-12 Hz oscillations occur. These probably result from excessive electrotonic coupling between dendrites of the inferior olivary neurons via GABA mediated gap junctions. The abnormal oscillations are transmitted via the Purkinje cells and Dentate/Interpositus nucleus and then distributed to thalamocortical and brainstem nuclei. 19-21 Clinical case reports of infarcts or lesions involving these pathways in ET patients have been shown to arrest tremor, (22-25).

The inferior olive is thought to play an important role as a teacher of the cerebellum in adjusting or modulating planned movements during their execution, in response to unconditioned afferent information. It achieves this by modulating cerebellar return to the motor cortex via the Purkinje cells, (26). Thus in ET patients, if there is excessive recruitment of inferior olive neurons in response to afferent information, and these neurons oscillate synchronously in the 4-12 Hz range, then this will have a potent effect on motor performance which will be manifested as tremor.

The dentate-interpositus fibers give collaterals to the ZI on way to the Vim nucleus of the thalamus and likewise the ZI feeds back to these deep cerebellar nuclei. High frequency DBS of the ZI will override these abnormal 4-12 Hz synchronized oscillations and arrest tremor. The inventor has observed that stimulating the ZI in a patient with ET improves both axial and distal tremor.

Deep brain stimulation is application of an electric field to an area of the brain. Deep brain stimulation may be applied by any method known to one skilled in the art.

DBS may be applied in such a way that the stimulation field applied to caudal ZI also stimulates the caudal STN. It is preferable that the anterior STN is not stimulated.

Preferably the stimulation field applied to the caudal ZI does not stimulate the medical lemniscus. The postero-medially placed medial lemniscus carries sensory information to the thalamus and stimulation of this area could cause parathesias. The stimulation field also preferably does not stimulate the internal capsule, which is laterally placed. Stimulation of the internal capsule could cause increased muscle tone. The stimulation field also preferably avoids stimulation of the red nucleus, which is placed medially. Stimulation of this area may produce cerebellar signs.

The area to which DBS is applied may preferably be identified using the Shaltenbrand Bailey Stereotactic Atlas of the Human Brain (27). The target site may preferably be identified on plate 54 LXXVIII H.V-3.5.7 mm posterior to the intercommisural line, and 14 mm lateral.

This area is lateral to that identified by Murata et al.

Preferably the step of applying DBS further comprises the step of introducing an electrode into the brain, such that the electrode is in contact with the caudal ZI. Any known DBS electrode may be used. The term "DBS electrode" refers to any electrical conducting lead for enabling the production of an electric field at a desired site suitable for use in DBS. Such electrodes are well known to those skilled in the art, for example those supplied by Medtronic, Inc., Minneapolis, Minn.

In addition, the method preferably further comprises connecting the electrodes to an electricity supply, in particular to a pulse generator. Any known pulse generator may be used, for example, those supplied by Medtronic, Inc., Minneapolis, Minn.

During DBS the electrode is used to produce an electric field at a desired target site. The electrode has a proximal end and a distal end, the proximal end being connected to a pulse generator. The proximal end is preferably connected to the pulse generator via an insulated wire. The distal end of the DBS electrode is positioned at the target site i.e. the caudal ZI, and an electric field generated.

The step of connecting the electrode to a pulse generator preferably includes providing the electrode on a lead having at least one conductor, and connecting the lead to the pulse generator; the method further comprising implanting the pulse generator in the body of the patient wherein the step of implanting the pulse generator the body of the patient comprises implanting the pulse generator in one of a cranial region or a pectoral region.

The electrode may be located at the target site by any known method. The method of the invention may be carried out, for example on an awake patient using micro electrode recording (MER) techniques, or on an anesthetized patient using MRI scanning. Such surgical methods are well known to those skilled in the art, any appropriate surgical method may be used.

The DBS is preferably applied at a mean voltage of between 1.0 and 3.0V.

DBS may be applied unilaterally or bilaterally, but is preferably applied bilaterally. Bilateral means that DBS is applied to both hemispheres of the brain. DBS is preferably applied bilaterally because PD usually affects both sides of the body, and is controlled by both sides of the brain.

DBS may be applied unilaterally, for example, when only one side of the body is affected, or when one side of the brain has already been treated.

Either a mono-polar or bi-polar electric field may be used. Preferably a mono-polar electric field is used.

Depending on the way the electrode is connected to the pulse generator, it is possible to create, for example, a mono-polar or a bi-polar electric field. Altering the connections of an electrode to a pulse generator is well known to those skilled in the art. In particular, the technical manual for Medtronic's DBS leads 3389 and 3387 clearly discusses changing electrical connections at the proximal end of an electrode to change the electric field generated at the distal end of the electrode.

In the method of the invention, DBS may be applied continually or intermittently. For example, DBS may be applied during only waking hours, or when required to control symptoms. DBS is preferably applied continuously.

Continuous application means that pulses of DBS are applied repeatedly without any significant lapses between pulses.

DBS pulses are preferably applied at a frequency of between 100 Hz and 200 Hz, most preferably between 130-180 Hz.

The invention also provides a method for identifying an area of a patient's brain to be targeted with deep brain stimulation for the treatment of Parkinson's disease, comprising the step of using a scan of a patient's brain to identify a target area in the caudal zona incerta.

Preferably the scan is an MR scan. On an MR scan the boundary of the STN and the red nucleus is preferably first defined using the Schaltenbrand Atlas as a visual guide. The target area is preferably postero-medial to the caudal ⅓rd of the STN.

Preferably the method of treating Parkinson's disease according to the present invention is carried out after the method of identifying a target area according to the invention Further provided by the invention is the use of deep brain stimulation of the caudal zona incerta in the treatment of Parkinson's disease.

Also provided is the use of a DBS electrode targeted to the caudal zona incerta in the preparation of a component for the treatment of Parkinson's disease.

The invention also provides a kit for use in treating Parkinson's disease comprising a DBS electrode and instructions for how to identify the caudal zona incerta. Preferably the kit also comprises instructions for how to position the DBS electrode at the caudal ZI during treatment.

The electrode preferably has a proximal end for connection to an electrical supply, and a distal end, which, in use, is positioned in contact with the caudal zona incerta.

BRIEF DESCRIPTION OF THE DRAWINGS

The invention will now be described in detail, by way of example only, with reference to the drawings in which.

DETAILED DESCRIPTION OF THE INVENTION

Examples

Figure 1:
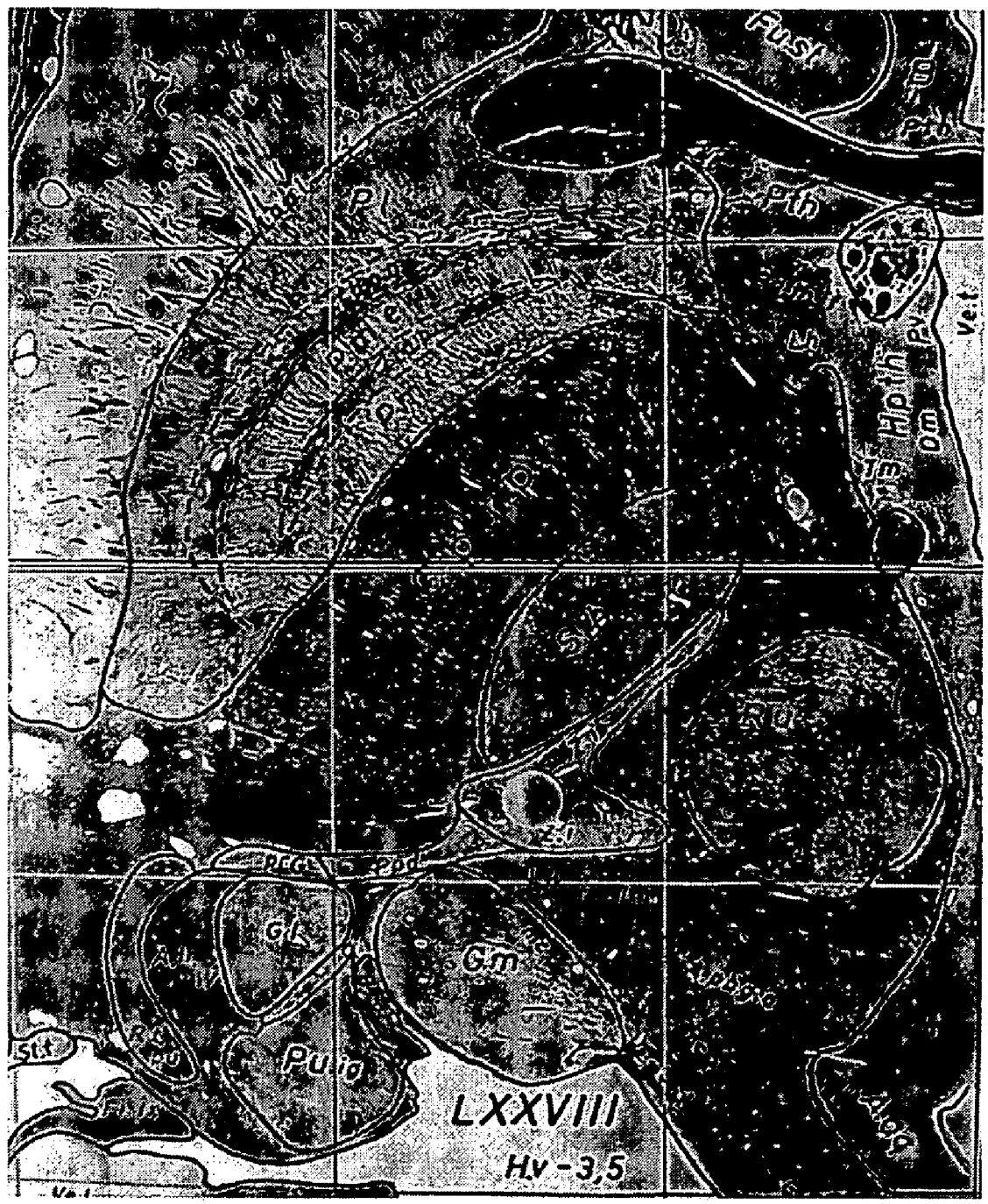
FIG. 1 is an axial view from the Schaltenbrand Atlas showing the position of the target area in the ZI.
Figure 2:
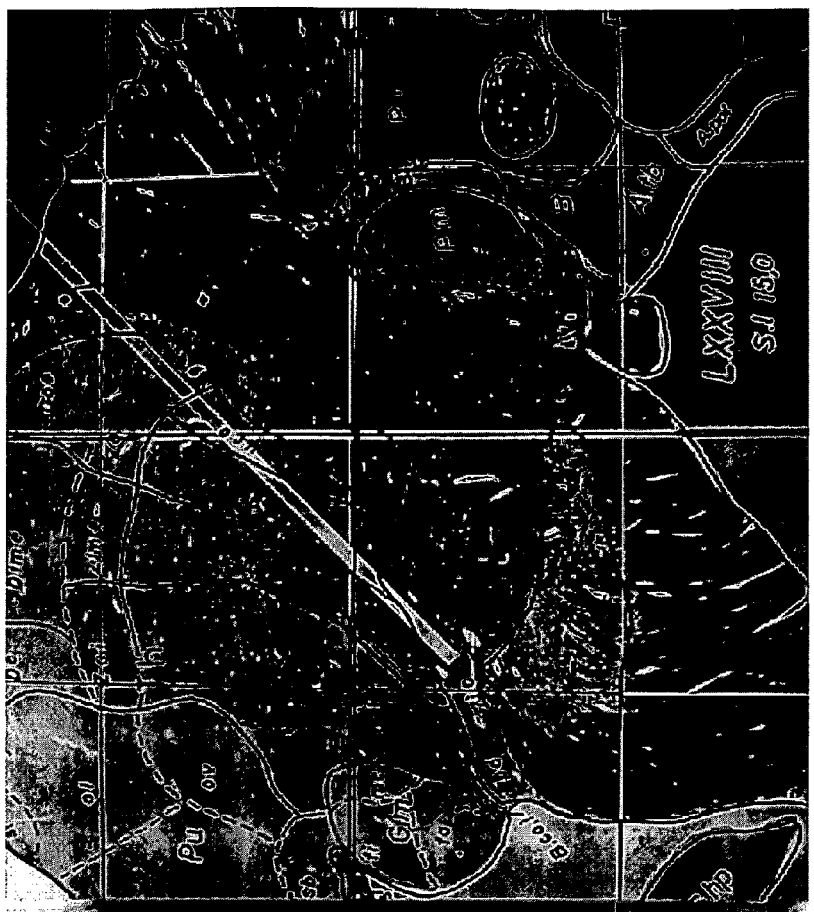
FIG. 2 is a sagittal per-operative MRI image showing a DBS electrode in the caudal ZI passing dorsally over the STN, and a corresponding sagittal slice from the Schaltenbrand Atlas.
Figure 2:
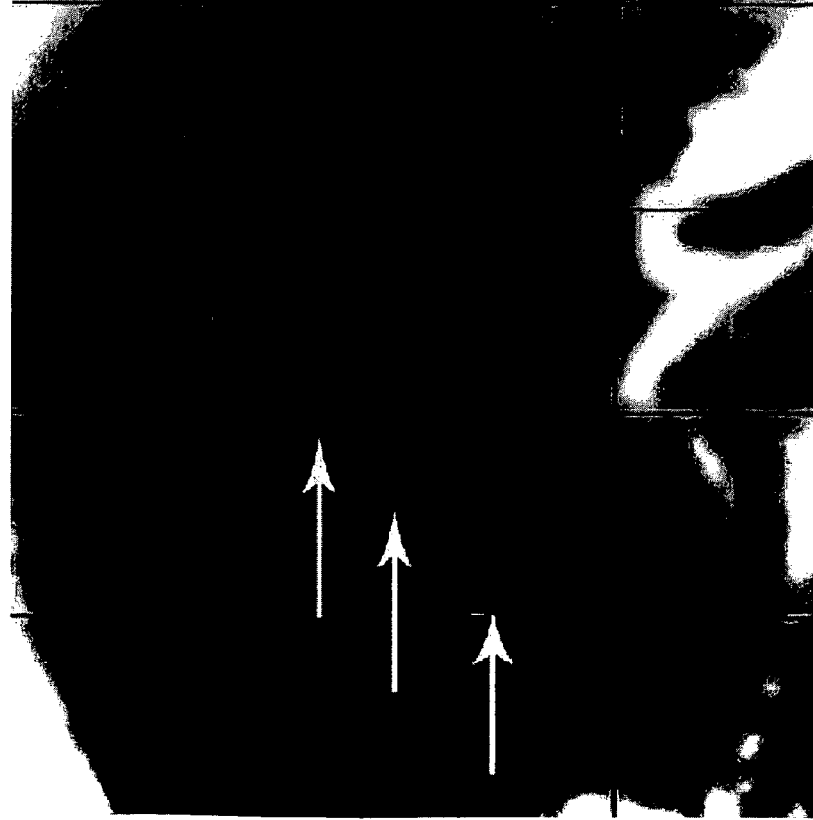
Figure 3:
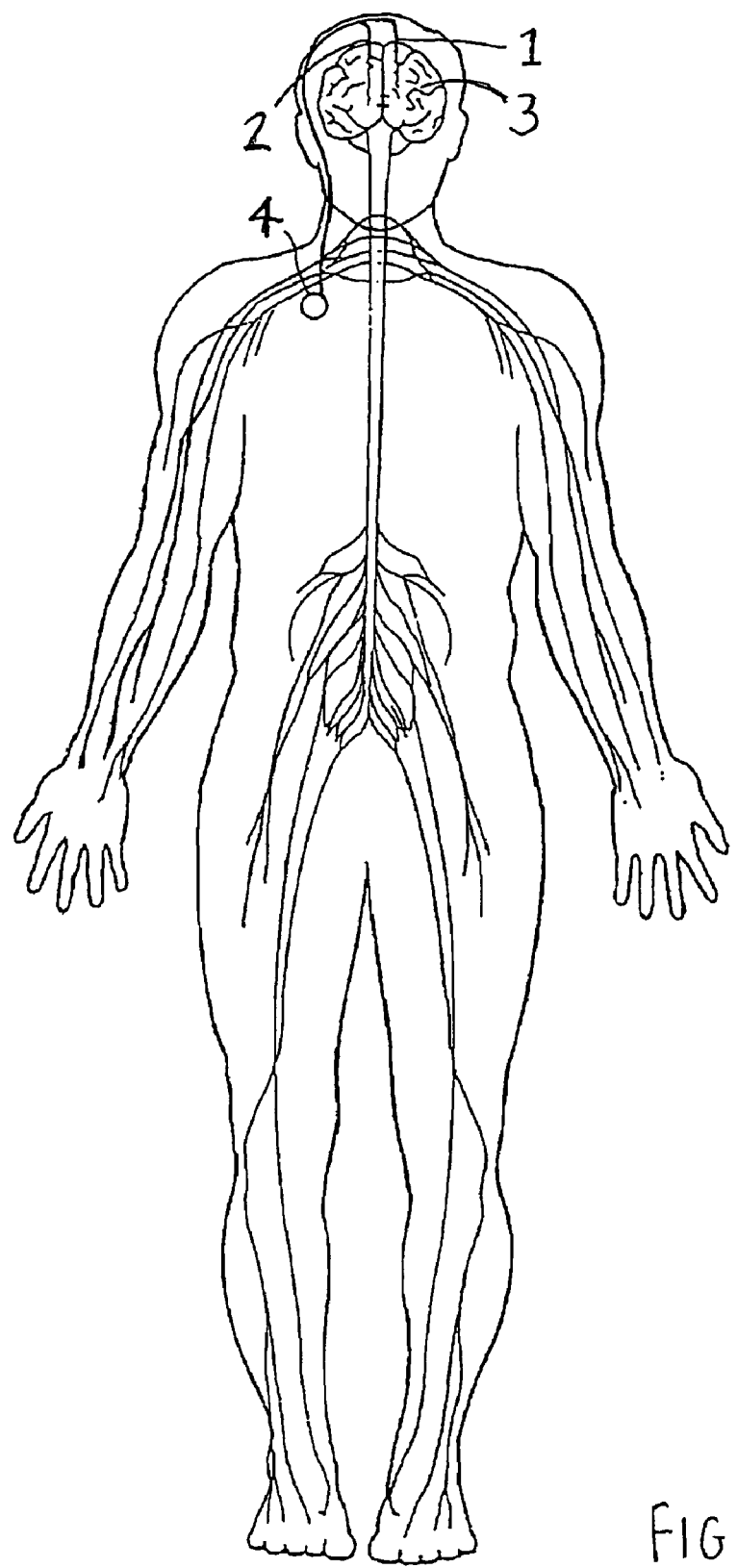
FIG. 3 is a diagram showing an electrode implanted into the target area, the electrode being connected to a pulse generator which is implanted into the patient's body.

The inventors have compared change in motor performance and dyskinesia for patients with PD, who have received DBS with therapeutic contacts in different locations in the subthalamic region to help define the optimum therapeutic site.

To implant a DBS lead into the ZI involves identifying the target on high resolution MR scans of the Subthalamic region acquired under strict stereotactic conditions. A stereotactic frame is applied to the head and a fiducial system is secured to it. The patient is then imaged with the stereotactic frame fixed within it and the target area can be determined on T2 weighted images that identify the STN and the Red nucleus. The inventor has found that the optimal MRI T2 sequences are 1.5 Tesla TR 2,500, TE 150, TSE 11, NSA 12. The identification of the target area can be assisted with reference to the Schaltembrand Atlas. The stereotactic coordinates of the Caudal ZI are then determined with reference to the fiducial markers that can be visualized on the image. The DBS lead (model 3389 DBS leads, Medtronic Inc., Minneapolis) has four contacts and to maximize the number of contacts placed within the Zona Incerta it is preferable to insert it with a 45 degree Antero-posterior trajectory with the second or third contact from tits target site. Stimulation current can then be applied to individual contacts or to a combination of contacts for bipolar stimulation to optimize the volume of current delivery for maximal therapeutic benefit. Structures which may be included in the field of stimulation in addition to the Caudal Zona Incerta may include the pallidofugal fibers, the posterior ⅓rd of the dorso-lateral part of the subthalamic nucleus (its exclusively motor component). Other neural pathways that would inevitably be included in the field of stimulation because they pass through the Caudal ZI include the afferents from the CM/Pf nucleus and dopaminergic afferents to the STN/ZI and basal ganglia. Stimulation of these structures would have a beneficial effect in the treatment of PD.

Example 2

35 patients with medically refractory idiopathic PD underwent MRI directed implantation of 64 quadripolar DBS leads (Model 3389 Medtronic Inc. Minn.) into the subthalamic region. There were 20 male and 15 females who together had a mean age of 60.5 years (SD 8.3 years). The platinum contacts on the DBS lead cause image artifact and so in order to determine the precise anatomical location of each contact on MRI, the inventors employed a delivery method using implantable plastic guide tubes (2). The technique is carried out under general anesthesia and involves advancing a guide tube over a probe that has been stereotactically delivered to the target so that the tube's distal end is short of the target and a hub on its proximal end is then fixed within the burr hole. The probe is removed and a radiopaque plastic stylette is introduced down the guide tube to the planned target and its position verified with per-operative MRI. The stylette is then withdrawn and replaced with a DBS lead at the same position which allows us to determine the exact anatomical position of each of its four contacts.

The dorsal half of the posterior third of the STN (sensory motor component) was initially targeted but we found that medially placed contacts had a greater therapeutic effect and so specifically targeted just medial to the STN in an area involving pallidofugal fibers and the Zona Incerta. Patients in this latter group with more posteriorly placed contacts showed further improvement and the inventors target subsequently moved to the Caudal Zona Incerta (see FIG. 1). The best "therapeutic" contact was determined postoperatively on programming by a nurse who remained "blind" to the preoperatively planned anatomical location of the DBS contacts. The 64 implanted DBS electrodes were divided into 3 groups based on the position of the active contacts; exclusively STN (17), medial to the STN (20) and exclusively caudal ZI (27). The primary outcome measure was the contralateral UPDRS III motor score (excluding gait and body bradykinesia which are affected by bilateral stimulation); secondary outcomes were scores for tremor, rigidity and bradykinesia (finger taps, hand movements, rapid alternating movements of hands and leg agility), timed hand movements, dyskinesia and total L-dopa dose. Each patient was assessed at follow-up (median time 6 months) off medication with the stimulator switched off ("off-off") or on ("on-off"). For most of the outcome variables, we used linear regression analysis to compare differences in on-off scores by procedure adjusting for disease severity using the off-off scores at follow-up, sex and age group (<55 years, 55 to 64 years, greater and equal to 65 years) with the STN patients as the reference group. The adjusted score differences, and 95% confidence interval, were converted to a percentage improvement relative to the STN off-off score (Table 1). 15 subjects were omitted from the analysis of the tremor score as their off-off tremor score was zero and they could not show improvement. We also used the ZI rather than the STN group as the baseline for the percentage improvement in tremor as the adjusted improvement for the ZI group would have resulted in a greater than 100% improvement due to the milder off-off scores for the STN group.

Discussion

This is the first study that demonstrates that locating the DBS electrodes posterior to the STN, within caudal ZI, is associated with greater improvement in overall motor scores than within the STN (76% vs. 55%); with a trend as one moves away from the STN (p<0.001). Tremor, rigidity and bradykinesia scores also showed a greater percentage improvement with a significant change in the timed hand movements (p<0.001). Consistent with these findings, we have previously reported that a subthalamic lesion that includes the ZI gives a better outcome than a lesion confined to STN. Neurons transmitting abnormal bursting activity and low frequency oscillations have been identified in the basal ganglia, thalamus, cortex and brainstem as well as in the ZI of patients with PD. The ZI receives input from the basal ganglia, the ascending reticular activating system (RAS) and associative and limbic areas of the brain, which facilitate and modulate motor behavior. It has excitatory output to the centromedian and parafascicular (CM/Pf) nuclei of the thalamus, which synchronizes neuronal firing in the striatum and the STN. It also feeds out directly to the cortex and locomotor centers in the brainstem. This is in contrast to the STN, which restricts its efferents to the basal ganglia output nuclei and the midbrain locomotor area. High frequency stimulation of the ZI is likely to have a more potent effect than STN in overriding the abnormal neuronal firing patterns that are found in PD due to its widespread efferent connections and therefore cause a greater improvement in motor symptoms.

Stimulation medial to the STN was associated with the best improvement in dyskinesia, possibly due to the involvement of the pallidofugal fibers. However, the inventors noticed that two out of five patients with bilateral stimulation in this region developed stimulation-dependent worsening of speech probably due to spread of current to the adjacent cerebello-Vim fibers thereby disrupting the transmission of information modulating fine motor control of the vocal cords.

All documents are incorporated herein by reference.

REFERENCES

1. Nagaseki Y, Shibazaki T, Hirai T, Kawashima Y, Hirato M, Wada H, et al. Long-term follow-up results of selective VIM-thalamotomy. J Neurosurg 1986; 65(3):296-302.
2. Mohadjer M, Goerke H, Milios E, Etou A, Mundinger F. Long-term results of stereotaxy in the treatment of essential tremor. Stereotact Funct Neurosurg 1990; 54-55:125-9.
3. Goldman M S, Ahlskog J E, Kelly P J. The symptomatic and functional outcome of stereotactic thalamotomy for medically intractable essential tremor. J Neurosurg 1992; 76(6):924-8.
4. Jankovic J, Cardoso F, Grossman R G, Hamilton W J. Outcome after stereotactic thalamotomy for parkinsonian, essential, and other types of tremor. Neurosurgery 1995; 37(4):680-6; discussion 686-7.
5. Selby G. Stereotactic surgery for the relief of Parkinson's disease. 2. An analysis of the results in a series of 303 patients (413 operations). J Neurol Sci. 1967; September-October; 5(2):343-75.
6. Rossitch E Jr Z S, Nashold B S Jr, Horner J, Walker J, Osborne D, Bullard D E. Evaluation of memory and language function pre- and postthalamotomy with an attempt to define those patients at risk for postoperative dysfunction. Surg Neurol. 1988; January; 29(1):11-6.
7. Tasker R R, Munz M, Junn F S, Kiss Z H, Davis K, Dostrovsky J O, et al. Deep brain stimulation and thalamotomy for tremor compared. Acta Neurochir Suppl (Wien) 1997; 68:49-53.
8. Schuurman P R, Bosch D A, Bossuyt P M, Bonsel G J, van Someren E J, de Bie R M, et al. A comparison of continuous thalamic stimulation and thalamotomy for suppression of severe tremor. N Engl J Med 2000; 342(7):461-8.
9. Benabid A L, Pollak P, Gao D, Hoffmann D, Limousin P, Gay E, et al. Chronic electrical stimulation of the ventralis intermedius nucleus of the thalamus as a treatment of movement disorders. J Neurosurg 1996; 84(2):203-14.
10. Pahwa R, Lyons K L, Wilkinson S B, Carpenter M A, Troster A I, Searl J P, et al. Bilateral thalamic stimulation for the treatment of essential tremor. Neurology 1999; 53(7): 1447-50.
11. Ondo W, Almaguer M, Jankovic J, Simpson R K. Thalamic deep brain stimulation: comparison between unilateral and bilateral placement. Arch Neurol 2001; 58(2):218-22.
12. Taha J M, Janszen M A, Favre J. Thalamic deep brain stimulation for the treatment of head, voice, and bilateral limb tremor. J Neurosurg 1999; 91 (1):68-72.
13. Benabid A L, Pollak P, Gervason C, Hoffmann D, Gao D M, Hommel M, et al. Long-term suppression of tremor by chronic stimulation of the ventral intermediate thalamic nucleus. Lancet 1991; 337(8738):403-6.
14. Hariz M I, Shamsgovara P, Johansson F, Hariz G, Fodstad H. Tolerance and tremor rebound following long-term chronic thalamic stimulation for Parkinsonian and essential tremor. Stereotact Funct Neurosurg 1999; 72(2-4):208-18.
15. Houeto J L, Mesnage V, Mallet L, Pillon B, Gargiulo M, du Moncel S T, et al. Behavioural disorders, Parkinson's disease and subthalamic stimulation. J Neurol Neurosurg Psychiatry 2002; 72(6):701-7.
16. Berney A, Vingerhoets F, Perrin A, Guex P, Villemure J G, Burkhard P R, et al. Effect on mood of subthalamic DBS for Parkinson's disease: a consecutive series of 24 patients. Neurology 2002; 59(9):1427-9.
17. Kulisevsky J, Berthier M L, Gironell A, Pascual-Sedano B, Molet J, Pares P. Mania following deep brain stimulation for Parkinson's disease. Neurology 2002; 59(9):1421-4.
18. Rajput A H, Rozdilsky B, Ang L, Rajput A. Clinicopathologic observations in essential tremor: report of six cases. Neurology 1991; 41(9):1422-4.
19. Wilms H, Sievers J, Deuschl G. Animal models of tremor. Mov Disord 1999; 14(4):557-71.
20. Deuschl G, Elble R J. The pathophysiology of essential tremor. Neurology 2000; 54(11 Suppl 4):S14-20.
21. Elble R. Central Mechanisms of Tremor. Journal of Clinical Neurophysiology. 1996; 13(2):133-144.
22. Dupuis M J, Delwaide P J, Boucquey D, Gonsette R E. Homolateral disappearance of essential tremor after cerebellar stroke. Mov Disord 1989; 4(2): 183-7.
23. Duncan R, Bone I, Melville I D. Essential tremor cured by infarction adjacent to the thalamus. J Neurol Neurosurg Psychiatry 1988; 51 (4):591-2.
24. Nagaratnam N, Kalasabail G. Contralateral abolition of essential tremor following a pontine stroke. J Neurol Sci 1997; 149(2):195-6.
25. Constantino A E, Louis E D. Unilateral disappearance of essential tremor after cerebral hemispheric infarct. J Neurol 2003; 250(3):354-5.
26. De Zeeuw Cl S J, Hoogenraad C C, Galjart N, Koekkoek S K, Ruigrok T J. Related Articles, Links, Review., MEDLINE] PP-if. Microcircuitry and function of the inferior olive. Trends Neurosci. 1998; September; 21 (9):391-400.
27. Murata J, Kitagawa, M, Uesugi H, Saito H, Iwasaki Y, Kikuchi S, Tashiro K, Sawamura Y. Electrical stimulation of the proximal subthalamic area for the treatment of intractable proximal tremor. J. Neurosurg 2003; 99: 708-715.

The invention claimed is:

1. A method of treating a movement disorder including the step of applying deep brain stimulation to the caudal zona incerta of the brain with an electric field that is sufficiently remote from the subthalamic nucleus to avoid stimulation of the anterior subthalamic nucleus, wherein said step of applying deep brain stimulation comprises the step of introducing an electrode into the brain, such that the electrode is in contact with the caudal zona incerta.

2. The method according to claim 1, wherein the step of introducing an electrode into the brain includes locating the electrode substantially at a location identified on the Schaltenbrand Bailey Stereotactic Atlas of the Human Brain, on plate 54 LXXVIII H.V-3,5.7 mm posterior to the intercomisural line, and 14 mm lateral.

3. The method according to claim 1, further comprising connecting the electrode to a pulse generator.

4. The method according to claim 3, wherein the step of connecting the electrode to a pulse generator includes: providing the electrode on a lead having at least one conductor, and connecting the lead to the pulse generator; the method further comprising implanting the pulse generator in the body of the patient wherein the step of implanting the pulse generator the body of the patient comprises implanting the pulse generator in one of a cranial region or a pectoral region.

5. The method according to claim 4, wherein the step of connecting the lead to the pulse generator includes connecting the lead to the pulse generator with a lead extension; the step of implanting the pulse generator in the body of the patient includes implanting the pulse generator in the pectoral region.

* * * * *